United States Patent [19]
Boiarski et al.

[11] Patent Number: 5,535,937
[45] Date of Patent: Jul. 16, 1996

[54] IDENTIFICATION DEVICE FOR SURGICAL INSTRUMENT

[75] Inventors: Anthony A. Boiarski, Columbus; Mark T. Byrne; Warren P. Williamson, both of Loveland, all of Ohio

[73] Assignee: Ethicon Endo-Surgery, Inc., Cincinnati, Ohio

[21] Appl. No.: 472,101

[22] Filed: Jun. 7, 1995

Related U.S. Application Data

[62] Division of Ser. No. 234,749, Apr. 28, 1994.

[51] Int. Cl.⁶ .................................................. A61B 17/068
[52] U.S. Cl. ..................... 227/175.3; 227/19; 227/176.1; 227/175.2; 227/180.1; 600/103
[58] Field of Search ...................................... 227/175, 176, 227/179, 19, 8, 175.1, 176.1, 178.1, 179.1, 19, 175.2, 175.3, 174.4, 180.1; 128/4

[56] References Cited

U.S. PATENT DOCUMENTS

| | | | |
|---|---|---|---|
| 4,907,588 | 3/1990 | Burston | 606/11 |
| 5,134,281 | 7/1992 | Bryenton et al. | |
| 5,151,085 | 9/1992 | Sakurai et al. | 604/22 |
| 5,383,880 | 1/1995 | Hooven | 227/175 |

FOREIGN PATENT DOCUMENTS

| | | | |
|---|---|---|---|
| 0408160A1 | 1/1991 | European Pat. Off. | A61B 17/36 |
| 0552050A2 | 7/1993 | European Pat. Off. | A61B 17/00 |
| 0552423A2 | 7/1993 | European Pat. Off. | A61B 17/072 |
| 0581400A1 | 2/1994 | European Pat. Off. | A61B 17/00 |
| 0630612A1 | 12/1994 | European Pat. Off. | A61B 17/00 |
| 0639349A2 | 2/1995 | European Pat. Off. | A61B 17/068 |
| 0679367A2 | 11/1995 | European Pat. Off. | A61B 17/072 |
| 4040537A1 | 8/1991 | Germany | B01J 19/10 |

*Primary Examiner*—Scott A. Smith
*Attorney, Agent, or Firm*—Susan M. Schmitt

[57] ABSTRACT

A device is provided for identifying certain characteristics of an end piece or end effector of a surgical instrument. A preferred embodiment provides a surgical stapling instrument having an electrical circuit contained on the stapling cartridge which is capable of indicating cartridge type and/or status (i.e., with or without staples) when a voltage or current is applied to the circuit.

22 Claims, 8 Drawing Sheets

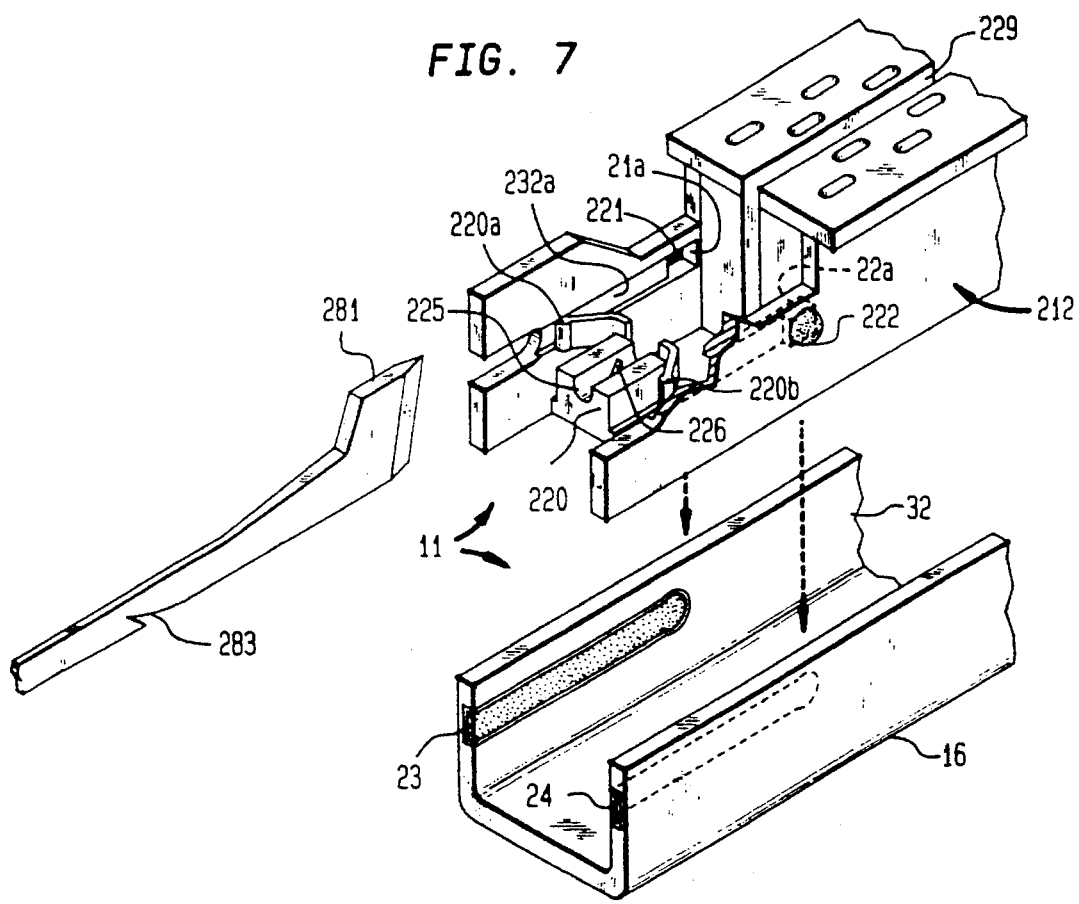
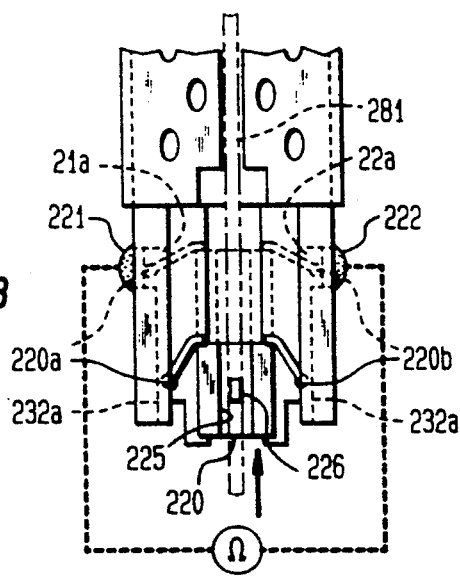

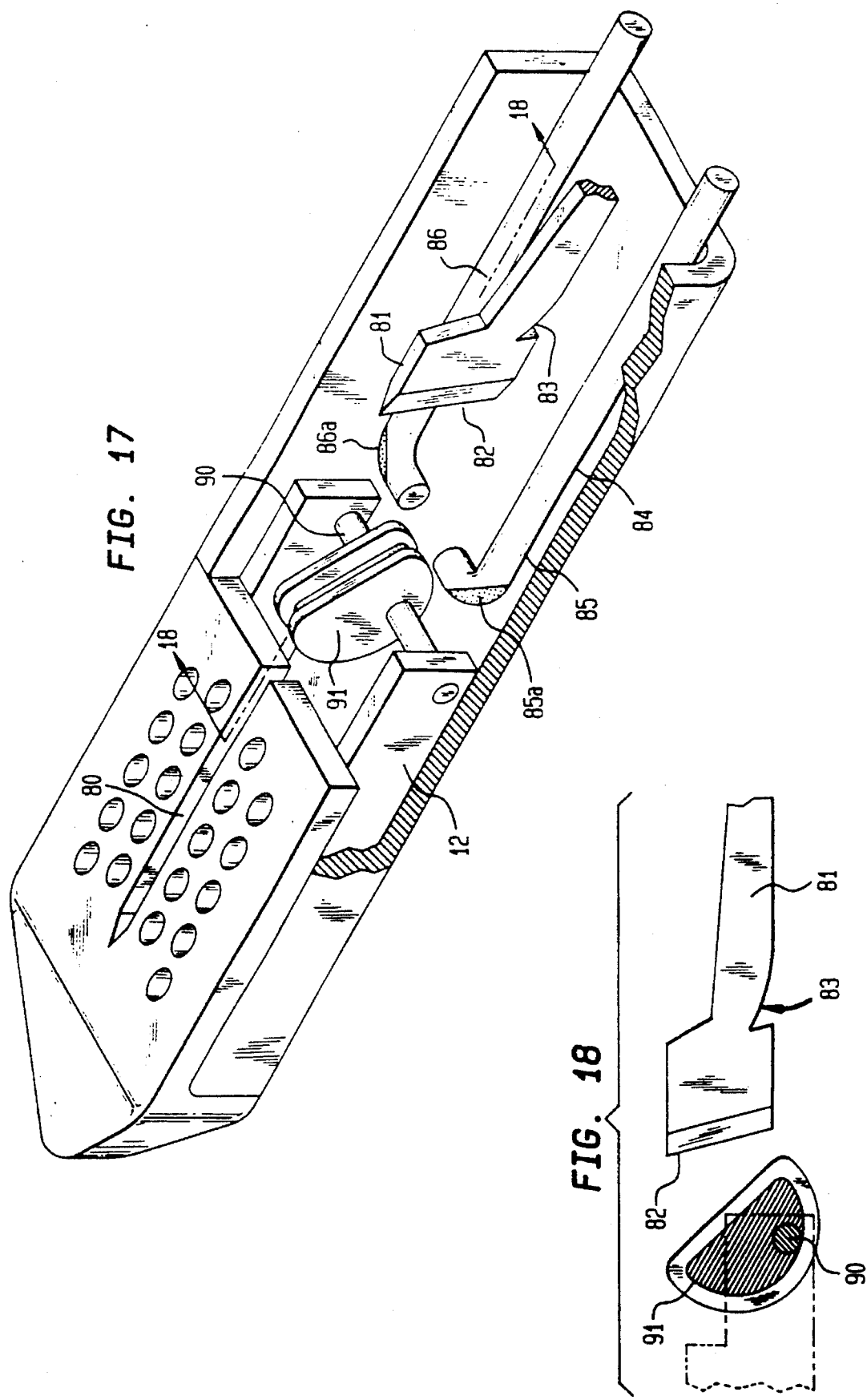

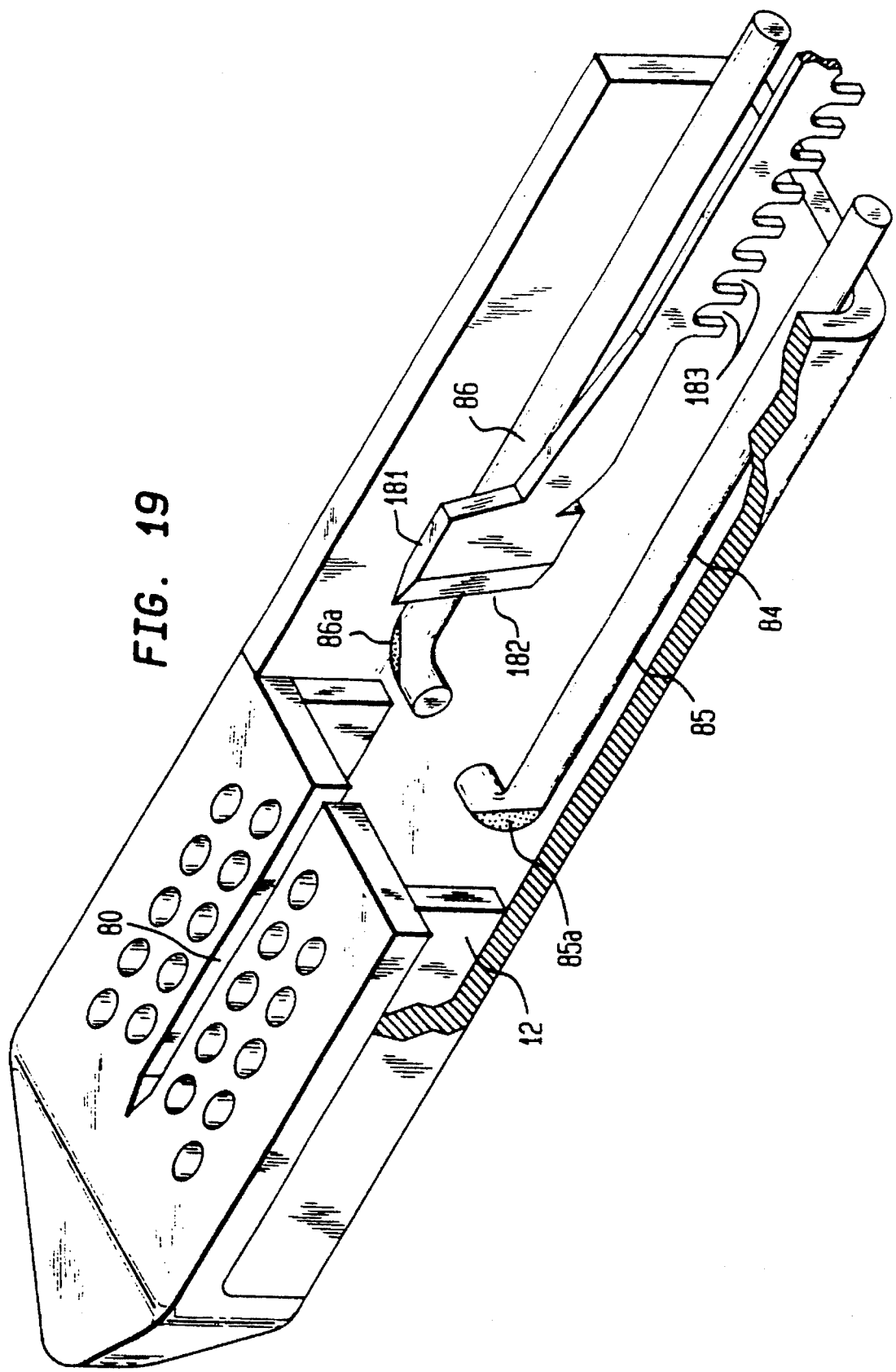

IDENTIFICATION DEVICE FOR SURGICAL INSTRUMENT

This is a division of application Ser. No. 08/234,749, filed Apr. 28, 1994, pending, which is hereby incorporated by reference.

FIELD OF THE INVENTION

This invention relates to a means for identifying certain characteristics of an end piece or end effector of a surgical instrument. One particular embodiment relates to the use of a means, for determining cartridge type and/or status, in an endoscopic cutting and stapling device.

BACKGROUND AND SUMMARY OF THE INVENTION

It is important for a surgeon to identify characteristics of instruments which are being used in a surgical procedure in order to determine whether the instruments are appropriate for their intended use.

Certain characteristics of the instrument may be obvious from viewing while others may not. For example, in an endoscopic surgical cutting and stapling instrument, whether an appropriate stapling cartridge is in place in a stapling device, or whether staples have been fired, may not be readily apparent from viewing the instrument. Also in the use of instruments having interchangeable end pieces for use with a common handle because the parts are interchangeable, specific replaceable instrument characteristic may not be apparent from viewing the reusable instrument handle. As the cost of producing and sterilizing instruments are taken into consideration, more disposable, replaceable instrument parts are being used, particularly in endoscopic surgery. As a result, more frequently, surgeons are using instrument end pieces which may be interchangeably attached to a reusable handle portion or the like. Particularly in endoscopic surgery, these instruments may present some instrument characteristic identification difficulties because the surgeon cannot see the instrument in a direct manner but is watching on a video display and manipulating the instrument based on what is seen in the display.

Accordingly, the present invention provides a means for identifying surgical instrument characteristics. The identifying means may be used to identify certain predetermined characteristics of an end piece of a surgical instrument. For example, an end piece of an instrument may have a shaft with an end effector on its distal end. The end effector and shaft may form a replaceable end piece which may be coupled or uncoupled from a handle. Alternatively, a portion of the end piece such as the end effector itself or a portion of the end effector may be replaceable. For example, a stapling cartridge, may be removable and replaceable.

The end piece may have a variety of characteristics such as end effector type or configuration, instrument length or size, or instrument status. The identifying means for determining end piece or end effector characteristics designates the specific characteristics to the user or control unit, for example, of an electromechanical powered instrument. Preferably the identifying means is integral with the end piece and preferably is located in the end effector or the distal or operative end of the instrument.

A preferred embodiment incorporates the identification means in a linear cutting and stapling instrument. A linear cutting and stapling instrument has end effector jaws which engage tissue and apply parallel rows of staples to secure and join layers of tissue while a cutting means cuts between the rows of staples. A cartridge containing the staples is located in an end effector at the distal end of the stapling device. Various types of cartridges may be used with the same instrument, depending on the particular application of the instrument. For example, depending on the predetermined tissue type or thickness, different cartridges may be used to vary the size of the gap between the two jaws of the end effector used to engage tissue for stapling.

It is important to know whether the appropriate cartridge for the particular tissue or application is inserted in the end effector. For example, if a cartridge for thicker tissue is used in thin tissue, the desired hemostasis might not occur and uncontrolled bleeding may result when the tissue is cut. If a cartridge with a smaller gap is used in fragile tissue such as lung tissue, the tissue may be torn or unnecessarily damaged.

It is also important to know whether the staples have already been fired from the cartridge or not so that the user does not inadvertently cut tissue without a means for providing hemostasis.

Therefore it is desirable to provide an identifying means for indicating cartridge type and/or indicating whether the cartridge still contains staples or has been fired.

Color coding to distinguish cartridge type has been used. Also, a mechanical means for indicating cartridge status has been described. Mechanical lockout means have been described, for example, in U.S. Pat. Nos. 4,892,244 and 5,129,570. The mechanical lockout means mechanically prevent instrument refiring unless a single shot staple cartridge has been replaced and the instrument reset. However, an electrical means for determining cartridge type or status has not been disclosed.

Accordingly, one aspect of the present invention provides a means, preferably electrical, for determining a cartridge type of a stapling device.

Another aspect of the invention provides a means for determining cartridge status, i.e., whether staples are still present in the cartridge. Cartridge status may be determined by detecting whether or not the instrument has been fired or how many times the instrument has been fired.

If a one-shot staple cartridge is used, a detection means needs only to determine whether or not the device has been fired with the existing cartridge in place. If a multifire staple is used, the detection means counts the number of times the device is fired.

The means for detecting instrument firing is preferably electrical as described in the Detailed Description below. However, other means are contemplated by this invention. For example a magnetic sensor may be located on a stationary portion of the device. A driver for advancing a cutting blade or firing staples may have a magnetic element which advances past and is detected by the sensor when the device is fired. If, for example, a multiple fire cartridge is used, the sensor communicates the firing to a control unit. The control unit contains a logic circuit which counts the number of times a device is fired. Other means for sensing cartridge firing may include, e.g., optical means. The present invention also provides a means for preventing the use of the instrument when a cartridge has been spent, i.e., when no staples remain.

Preferably the present invention is incorporated into an instrument using electrical energy for other purposes, e.g., for cutting or cauterization or to provide electromechanical energy for instrument positioning and/or staple firing such as in an electromechanical cutter.

With increasing automation in surgery, it may be necessary for an instrument control unit in an automated device to be capable of recognizing certain predetermined instrument characteristics. An example of such a device is an electromechanical cutting and stapling device in which a control unit sequences the steps of electromechanically assisted instrument use. The control unit, or controller assists the stapling and cutting functions of the instrument by directing a suitable power means to operate the business head or end effector of the instrument to conduct a desired step in the procedure. The power source sends an electrical signal which is translated into electromechanical energy preferably either by or through a shaft. In preferred embodiments, the shaft is encased in a housing and a motion is provided to the shaft, i.e., rotation, longitudinal movement, etc. Means are disposed in the end effector to translate the motion of the shaft into a suitable force and/or motion in the head to carry out a desired step, i.e., to set and form staples or to sever tissue, etc. Examples of electromechanical cutters are described in U.S. Ser. Nos. 07/822,478, 07/991,619 and 08/91,807 incorporated herein by reference. An improved electromechanical cutter would recognize, e.g., whether the staple cartridge is appropriate for the tissue thickness and type of tissue it is intended to cut and staple.

Thus, one embodiment of the present invention, provides a means for determining instrument characteristics in an electromechanical cutter. A preferred embodiment provides an electromechanical device having a control unit for sequencing the steps of instrument use which also identifies the instrument characteristics. An electromechanical cutter is preferred in which the control unit uses means to identify the cartridge type and determine whether the staples have been fired. If the cartridge is inappropriate or the staples have been fired, then instrument use is locked out with a lock-out means. For example, the lock-out means may be contained in the logic of the control unit of an electromechanically powered stapling device. The control unit will not cause the device to fire if the electrical means indicates an inappropriate or fired instrument status. In one embodiment where a cutting device is used, the lock-out prevents advancing of the cutting blade with an inappropriate or spent cartridge.

An alternative means for determining instrument characteristics provides optical means for determining instrument characteristics. One embodiment provides light emitted from a control unit and reflected by the instrument. The light is sensed and converted into an electrical signal, e.g., using a photodiode associated with the control unit. The reflected light indicates a predetermined instrument characteristic for the particular reflected light signal. For example a different cartridge type would reflect light having a different intensity or wavelength.

Alternatively a discrete number of reflected light outputs either transmitting or blocking light, interface with a discrete number of light sensors which sense the transmitted light. The resulting light outputs have an on or off status (reflecting or blocking) thus representing a binary code preset to indicate specific end piece characteristics. An advantage of the optical means is the shaft portion including the light input surface, light pipe, and output lenses are capable of withstanding preferred radiation sterilization methods.

These and other objects of the invention will be better understood from the following Detailed Description of the Drawings and Detailed Description of the Invention.

DETAILED DESCRIPTION OF THE DRAWINGS

FIG. 7 illustrates a partial perspective view of an alternative cartridge of the present invention;

FIG. 8 illustrates a partial top view of the cartridge of FIG. 7;

FIG. 17 illustrates a perspective view of a distal end of an alternative embodiment of the instrument of FIG. 1 including an optical lockout means;

FIG. 18 illustrates a side cross-sectional view of the instrument of FIG. 16 along the lines 18—18; and FIG. 19 illustrates a perspective view of an instrument having an alterative optical lockout means included with cutting means.

DETAILED DESCRIPTION OF THE INVENTION

Figure 1:
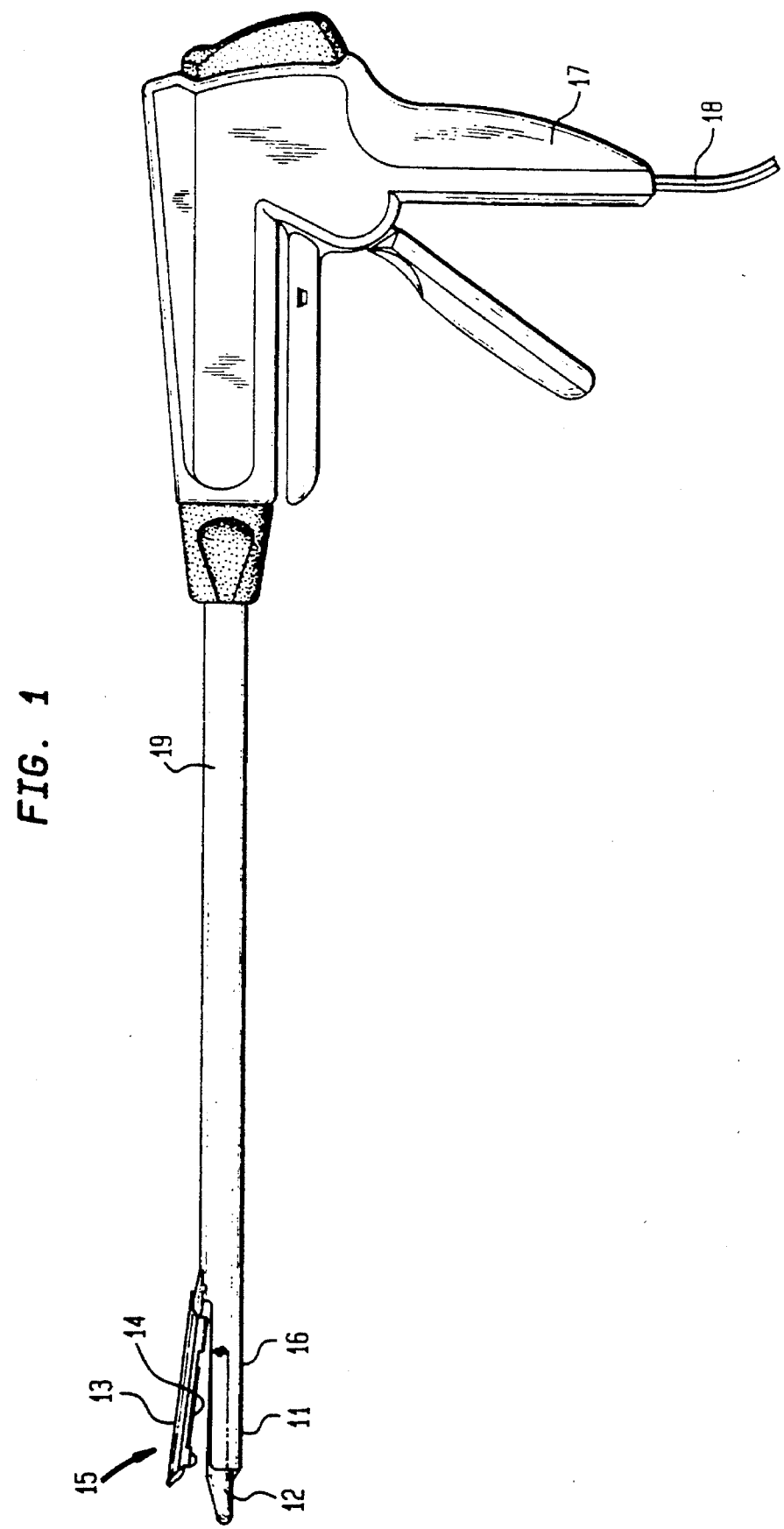
FIG. 1 illustrates a linear cutting and stapling instrument.
Figure 2:
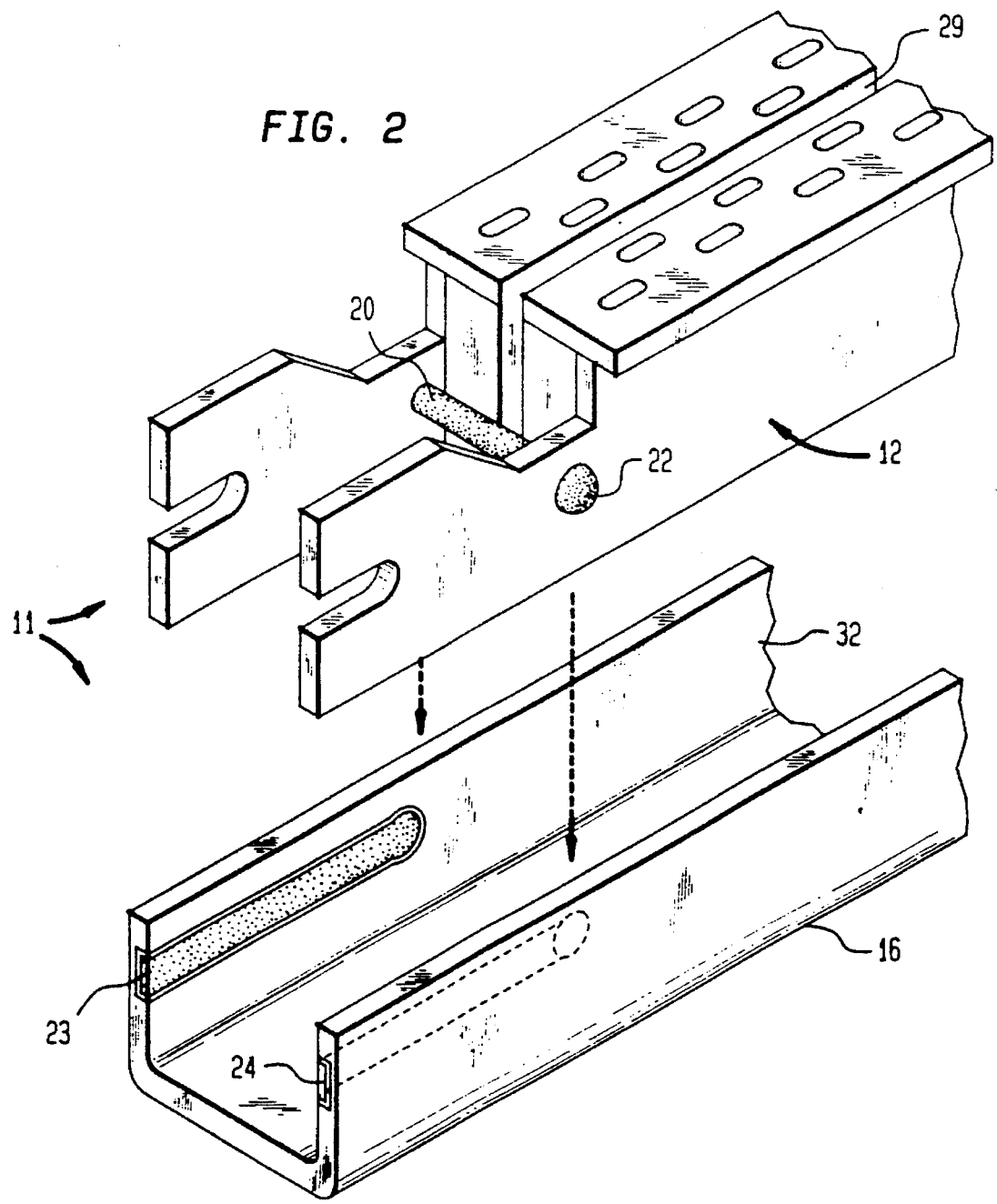
FIG. 2 illustrates an exploded partial perspective of a cartridge holder and cartridge of a first embodiment of the invention.
Figure 3:
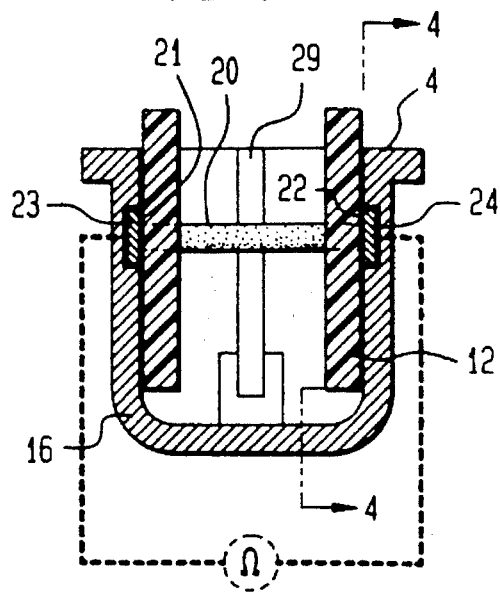
FIG. 3 illustrates a front cross section of the cartridge holder and cartridge of FIG. 2.
Figure 4:
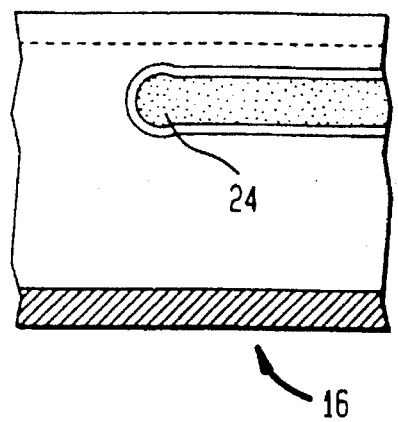
FIG. 4 illustrates a cross section along the lines 4—4 of FIG. 3.
Figure 5:
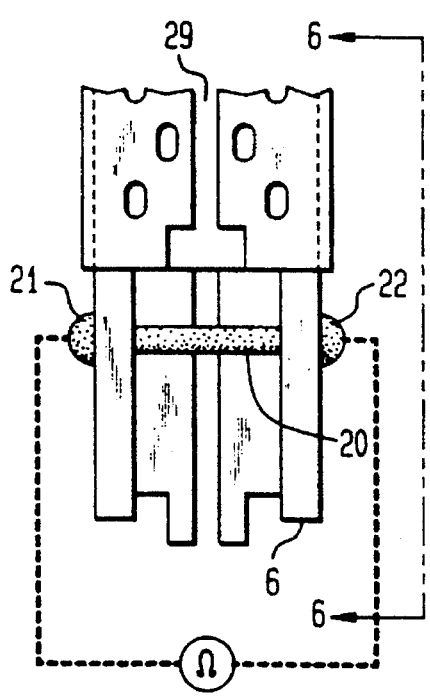
FIG. 5 illustrates a partial top view of the cartridge of FIG. 2.
Figure 6:
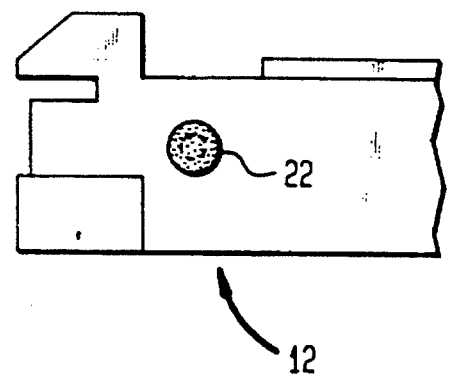
FIG. 6 illustrates a cross section along the lines 6—6 of FIG. 5.

FIG. 1 illustrates a linear cutting and stapling device 10 having a handle portion 17 coupled to a shaft 19 having an end effector 15 on its distal end. The end effector 15 has two jaws 11, 13 between which tissue may be engaged for cutting and stapling. The top jaw 13 comprises an anvil 14 for receiving and forming staples. The lower jaw 11 comprises a cartridge holder 16 and a cartridge 12 insertable into cartridge holder 16. Operation of linear cutting and stapling instruments are known in the art and are discussed, for example, in U.S. Pat. Nos. 4,608,981, 4,633,874, and U.S. application Ser. No. 07/917,636 incorporated herein by reference.

An electrical energy communication means comprises wires 18 which enter the instrument 10 through the handle 16 and communicates with a circuit in lower jaw 11. Wires 18 are coupled to a control unit (not shown) including a generator which supplies energy to the circuit.

In FIGS. 2–6 there is illustrated a first embodiment of a linear cutting and stapling device. The cartridge 12 is illustrated inserted into the cartridge holder 16 in FIG. 3. The cartridge 12 has an electrically conductive ribbon 20, such as a metallic foil, positioned across a knife slot 29 extending longitudinally through the cartridge 12. An electrical circuit integral to the cartridge includes the conductive ribbon 20 acting as a mechanically actuated fuse, and electrical contacts 21, 22 on each side of the ribbon 20. Conductive strips 23, 24 are located on inner walls 32 of cartridge channel 16 and make electrical contact with contacts 21, 22 respectively when cartridge 12 is inserted in channel 16. Alternatively, conductive strips may also be located on outer wall or within cartridge channel. Conductive strips 23, 24 are coupled to wires 18 through which electrical energy is provided to the circuit and are electrically isolated from the cartridge channel using appropriate insulation.

If the cartridge 12 is inserted in the cartridge channel 16, the ribbon 20 is in place, and electrical energy is applied to the circuit, an electrical signal appears at the output indicating that the instrument is ready to fire. When the instrument is fired, a knife moves forward, through the knife slot 29 to cut tissue engaged between jaws as staples are being applied. The ribbon 20 is cut as the knife moves through the knife slot 29. When the ribbon 20 is cut, the circuit is opened. Thus, when electrical energy is applied, no signal appears across the circuit, thereby indicating that the knife has been moved through the knife slot, i.e., that the instrument has been fired.

FIGS. 7 and 8 illustrate an alternative cartridge 212 to be used in conjunction with the cartridge channel of FIGS. 2–4 and 6. The cartridge 212 is inserted to fit within a cartridge channel as illustrated in FIGS. 2–6. The cartridge 212 includes contacts 221, 222 which are in contact with conductive strips 23, 24 of the cartridge channel 16 when inserted into the channel 16 for use.

The cartridge 212 includes side walls 232 having grooves 232a. The cartridge 212 also includes an electrically conductive tab 220 having electrically conductive ears 220a, 220b, biased laterally from each other such that ears 220a, 220b, are slidable within grooves. The distal end of the grooves include contacts 221 and 222 having holes 21a, 22a.

The instrument includes cutting element 281, with a cutting blade 282 located on its distal end which may be passed through knife slot 229. The use of such cutting elements is known in cutting and stapling instruments in the art. Typically, such cutting element is coupled to an actuating element associated with a handle of an instrument. Such devices are described, for example, in U.S. Pat. No. 4,608, 981 and 4,633,874. The cutting element 281 also includes a notch 283 on its under side.

The tab 220 also includes a slot 225 through which the knife 281 may pass as the instrument is actuated. The slot 225 includes a catch 226 which engages with the notch 283 of the knife. After the notch 283 engages with catch 226, the knife continues to advance until the blade stroke is completed. As the knife or cutting element 281 is advanced distally, the notch on the knife couples with the tab 220 and advances the tab 220 distally until the ears 220a, 220b contact contacts 221, 222. The tab 220 thereby closes a circuit which includes conductive strips 23 and 24 and contacts 221, 222. The circuit is initially open until the device is actuated. The closed circuit provides an electrical signal indicating that the instrument has been fired. The tab 220 and notch 283 on the knife 281 are arranged so that the circuit will close at the end of the blade stroke. The tab 220 remains in place with conductive ears 220a, 220b engaged in holes 21a, 22b at contacts 221, 222, when the knife is retracted. Thus, when the cartridge is spent the tab will remain in its advanced position.

Figure 9:
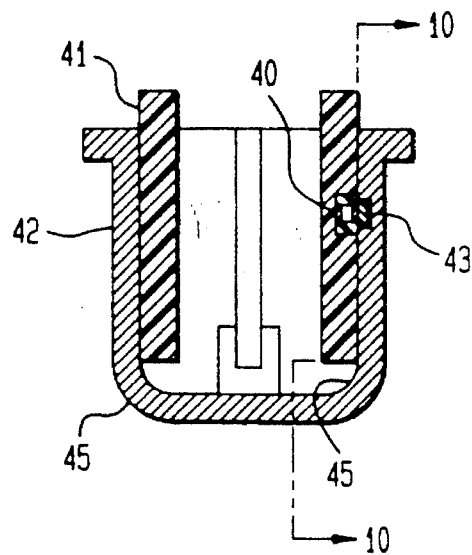
FIG. 9 illustrates a front cross section of a cartridge holder and cartridge of another of the invention.
Figure 10:
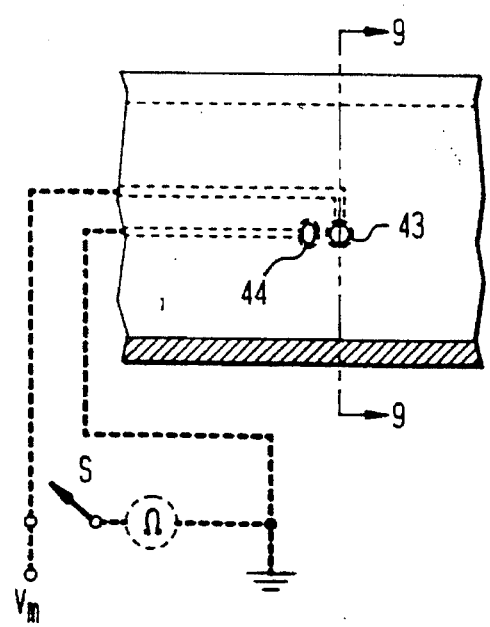
FIG. 10 illustrates a cross section of FIG. 9 along the lines 10—10.
Figure 11:
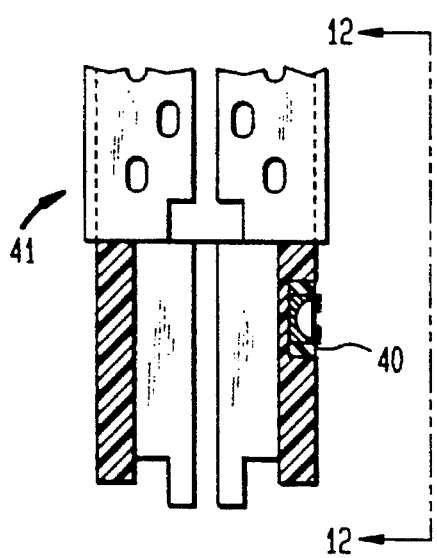
FIG. 11 illustrates a top partial view of the cartridge of FIG. 9.
Figure 12:
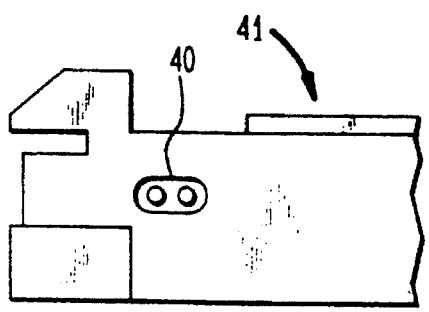
FIG. 12 illustrates a cross section of FIG. 11 along the lines 12—12.

In FIGS. 9–11 there is illustrated cartridge 41 and cartridge channel 42 of another embodiment of a linear cutting and stapling device. The cartridge 41 is comprised of a fuse 40 which is included in a circuit integral with the cartridge 41 and cartridge channel 42. A current may be applied to the circuit to measure a voltage across the circuit. Of course the current applied to determine a voltage across the circuit must not exceed the fuse's design limit so as not to blow the fuse and open the circuit. The cartridge channel 42 has conductive strips 43, 44 which are located on inside walls 45 of cartridge channel 42 and are electrically isolated from the walls 45 with insulation. The fuse 40 is in electrical contact with conductive strips 43, 44 on each side of the fuse 40 respectively. The conductive strips 43, 44 are also in electrical communication with an electrical energy source (not shown), which may deliver a current to the circuit. When the device is fired, a current is delivered to the circuit, synchronous with the cutting and staple forming action. This current is sufficiently above the design limits of the fuse to cause the circuit to break. Thus, when the device has been fired and the staples used, there will be no electric continuity of the circuit and a zero voltage will appear across the circuit.

Figure 13:
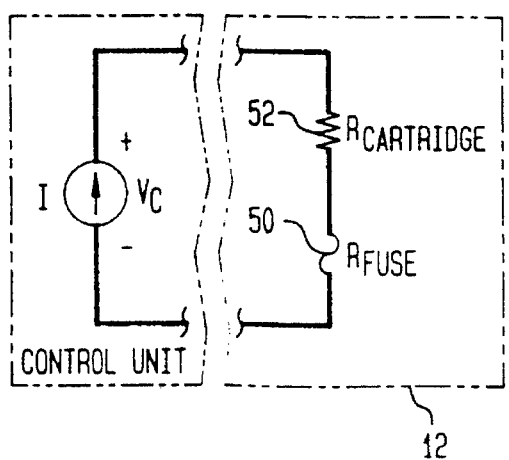
FIG. 13 illustrates a circuit diagram of a circuit integral with a cartridge of a third embodiment of the invention.

In FIG. 13 there is illustrated a circuit diagram of a third embodiment of a linear cutting and stapling device. In this device the electrical means serves a dual purpose of identifying the cartridge type and indicating whether the instrument has been fired.

The cartridge comprises a fuse 50 and an impedance element 52. In this embodiment, the impedance element is in series with the fuse 50. The fuse 50 has a known small resistance, $R_f$, preferable about 0.2 ohms. The impedance element 52 may be a resistor if, for example, a DC current is used, or a capacitor if an AC current is used. An inductor also may be used with an AC current source in which case the inductor is arranged in parallel with the fuse 50.

The impedance element 52 is preferable of a high resistance value $R_c$ as compared to $R_f$, or high impedance value $Z_c$ as compared to $Z_f$. Hence the voltage across the circuit, $V_c$ is approximately equal to $IR_c$ or $IZ_c$ respectively. A low current may be applied across the impedance element 52 to determine its value without blowing the fuse. The value of the impedance element corresponds to the cartridge type. The resistance value for $R_c$ or impedance value for $Z_c$ is preset to correspond to a particular one of a number of different cartridges types. The values of the impedances for the various cartridge types are carefully spaced so that the various cartridges can be distinguished. For example, in one embodiment, the $R_c$ values are 5, 50, and 100 ohms for three different tissue thickness ranges. In this particular example the current is preferably about 1–10 mA.

The fuse will not blow when a known first current of $I_1$, is delivered through the circuit. When $I_1$ is applied, the voltage across the circuit is measured. In the embodiment using DC current, the resistance $R_c$ is calculated from the known current and $R_f$ values; and the measured voltage. In the embodiment using AC current, the impedance, $Z_c$, of the impedance element may be determined from the magnitude and phase relationships between the current, $I_1$, through the circuit and the voltage across the circuit.

An indicator means may be used to indicate to a user or a control unit, which cartridge is being used, for example, for thin, regular or thick tissue. The indicator means may be visual, in the form of an annunciator light on the instrument itself, or, in the preferred embodiment, via a text overlay on the video monitor the surgeon watches while performing the procedure. If the cartridge is identified as an appropriate cartridge for the intended application, the instrument may be manipulated to engage tissue to be cut and the instrument fired. As the instrument is fired the staples are applied, the knife is advanced and a current $I_2$, sufficient to blow the fuse, is applied. Obviously, $I_2$ is higher than $I_1$. In this particular example the current, $I_2$, is about 100 mA. After the fuse has been blown, a zero voltage will appear across the circuit when energy is applied, indicating a fired cartridge status.

Alternatively, the cartridge may comprise an impedance element which acts as a fuse. The impedance element has a resistance or impedance preselected depending on the cartridge type, which may be measured by applying a current below the impedance element's design tolerance. This embodiment operates as the third embodiment described above except that the function of fuse and resistor or impedance element is combined into the impedance element.

Alternatively, in the case of the moving knife cutting the conductive foil, (FIGS. 2–6) the foil may be produced with a known impedance value corresponding to a particular cartridge type.

In an electromechanically controlled instrument, firing is prevented by the internal logic of the control means unit. If an inappropriate value of resistance or an open circuit is detected for the desirable application, the control means inhibits the firing of the instrument. The control means may be incorporated into the device or may be separate and external to the instrument.

Figure 15:
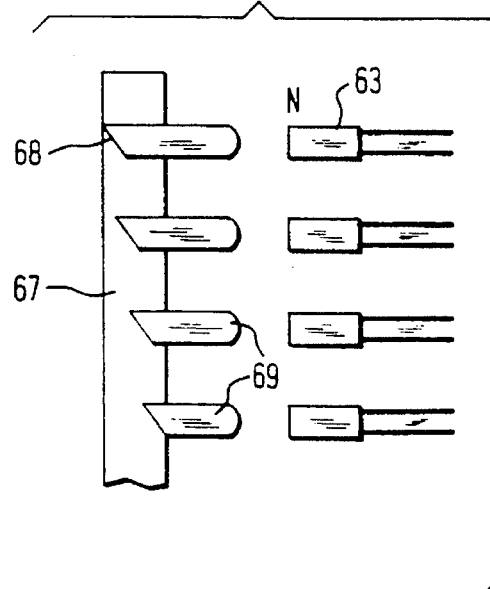
FIG. 15 is an enlarged view of the light outputs and sensors of an optical indication means.
Figure 14:
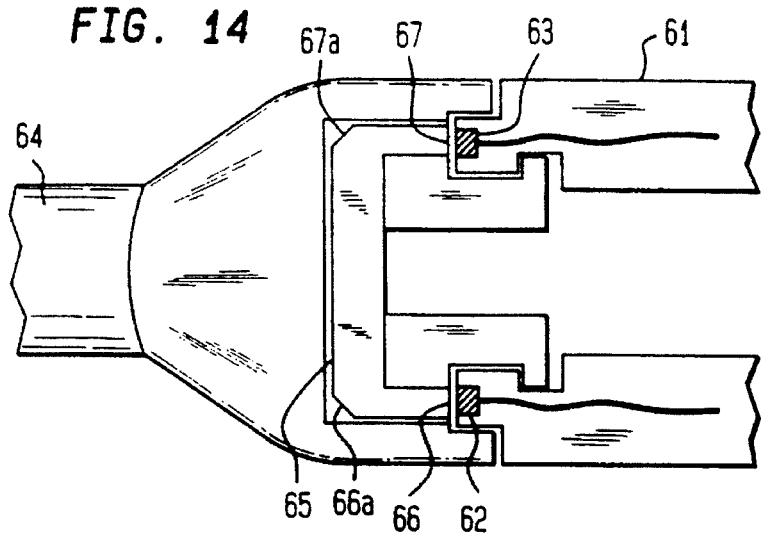
FIG. 14 illustrates an alternative of the present invention in which a optical means indicates specific instrument characteristics.

An alternative embodiment is shown in FIGS. 14 and 15 in which an optical means is provided for determining instrument characteristics. A handpiece 61 includes on its distal end, a light source such as an LED 62, and a series of light sensors 63 such as photodiodes. In FIG. 14 a single light output 67 and light sensor 63 is illustrated. In FIG. 15 a plurality of light outputs and light sensors is schematically shown. A disposable shaft 64 is removably coupled to the distal end of the handpiece 61. The shaft 64 includes an end effector (not shown) on its distal end and a light guide 65 on its proximal end. The light guide may be constructed in various shapes depending on the desired light transmitting effect. In the embodiment illustrated in FIG. 14, the light guide 65 comprises a tubular member having a first facet 66 and a second facet 67 and is constructed from a light transmitting material which transmits light of predetermined wavelengths, e.g., infrared light. The first light facet 66 includes a first reflective surface 66a and the second light facet 67 includes a second reflective surface 67a. The reflective surfaces 66a, 67a reflect the incident light in a desired direction.

For transmission of broad bandwidths of light, the light guide may be constructed of a material such as, for example, glass, polycarbonate or polysulfone. The light guide may be designed to act as a filter to filter out unwanted light. A narrow bandwidth of wavelengths of light may be used as well, to identify instrument characteristics.

The shaft 64 is coupled to the handpiece 61 so the first facet 66 is capable of receiving light emitted from LED 62. Light passing through the guide 65, is reflected at right angles to the axis of the guide 65 by reflective surfaces 66a and 67a. The reflection causes light to exit at a desired facet. The second facet 67 is in communication with the sensor(s) 63 so that a portion of light transmitted through the light guide 65 may be received by the sensor(s) 63.

In FIG. 15, a series of light outputs 69 is associated with the second facet 67. A series of reflective surfaces 68 is associated with the series of light outputs 69 such that each reflective surface 68 reflects a portion of light traveling through the light guide towards a corresponding light output 69. Each of the light outputs 69 is associated with a corresponding light sensor 63 so that the light output 69 communicates light to the corresponding sensor 63. Each light output 69 either transmits light or blocks light so that each output communicates one of two signals to a corresponding sensor, i.e., either light "on" or "off". The sensors 63 thus convert the light signals into a binary coded electrical signal.

The possible number of variations of signals and thus kinds of instruments or instrument characteristics which can be recognized by the instrument identification device is equal to $2^n$ where N is the number of light sensors. The resulting electrical signal may be communicated to a microprocessor which may interpret the data and respond appropriately. Preferably the sensors, data base and microprocessor are associated with a reusable handle portion of an instrument and the light input, reflective surfaces, and outputs are associated with a disposable instrument end piece.

An alternative embodiment of the optical identification means provides a sensor or sensors which comprise a material having a predetermined reflectivity, i.e., index of light refraction, transmission of a particular light component, or has a specific light built into the device using variables such as shape and/or material, which corresponds to one or more characteristics of the shaft or end piece coupled to the shaft. The sensor detects the amount of light, i.e., the incident optical power, and emits an electrical signal which corresponds to the predetermined device characteristics.

Figure 16:
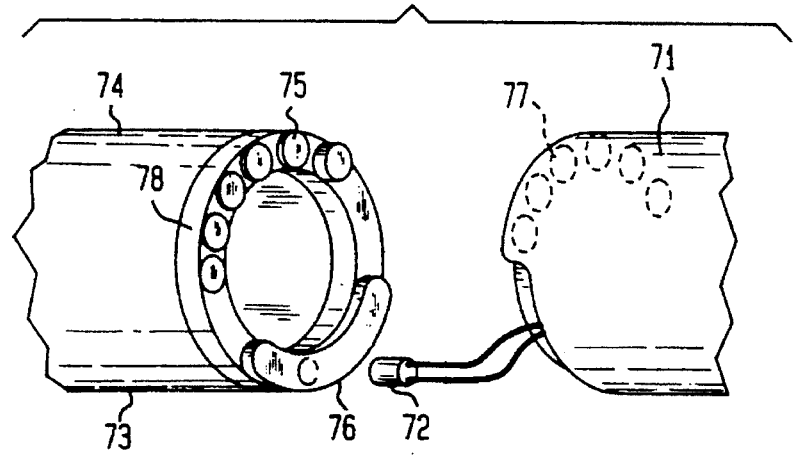
FIG. 16 illustrates a perspective view of a proximal end of an instrument shaft including an alternative embodiment of optical means.

Another variation of an optical means for indicating device characteristics is illustrated in FIG. 16. The optical means comprises a light source 72 associated with a handle portion 71 for emitting light to an input surface 76 on a circular shaped interfacing shaft 73 of an end piece 74. The shaft 73 has a discrete number of output lenses 75 which interface with a discrete number of light sensors 77 associated with a circular distal end of the handle portion 71 which interfaces with the shaft. The input surface 76 is coupled to the output lenses 75 by way of a light pipe or guide 78, such as an optic fiber. The output lenses 75 individually either block light or reflect the light. The ability to block or reflect light is built into the shaft on the end piece, for example, by using reflective surfaces molded into the light pipe. The result is a binary codedlight output which is preselected to depend on specific end piece characteristics.

Another embodiment of the optical identification means of the present invention is illustrated in FIGS. 17 and 18 in use with the linear cutting and stapling instrument of FIG. 1. The optical means includes an optical path and an optical path interruption means for physically interrupting transmission of light through said optical path to indicate an instrument state.

A perspective view of the end effector of the linear cutting and stapling instrument of FIG. 1 is shown in FIG. 17. The cartridge 12 inserted into jaw member 11 includes a knife channel 80 extending longitudinally through the center of the cartridge 12. A cutting means 81 is slidable through the knife channel 80. The cartridge 12 also includes a flag member 90 rotatably attached on each side of the cartridge 12 at the proximal end of the cartridge 12, and perpendicular to a plane defined by the knife channel 80. The flag member 90 includes a flag 91 having two positions, an up position and a down position. The flag 91 in the up position is situated at least partially in the knife channel 80.

The cutting means 81 includes a blade 82 with a notch 83. Before or as the cutting means is actuated, the instrument applies longitudinal parallel rows of staples along either side of the cut line. As the cutting means 81 is extended distally through the knife channel 80, the cutting means 81 passes over the flag 91 in the up position. When the cutting means is retracted, the notch 83 engages the flag 91 rotating it from the up position to the down position.

Jaw member 11 further comprises a light guide 84 comprising two parts, a transmitting portion 85 and a return portion 86. The transmitting portion 85 is coupled at the proximal end of the instrument, to a light source, extends distally through the shaft 19 and has a reflective surface 859 on its distal end for bending light in a desired direction. The return portion 86 is coupled at the proximal end of the instrument to a light sensing means, extends longitudinally through the shaft 19 on a side opposite the knife channel 80 of said jaw member 11 and has a reflective surface on its distal end. The transmitting portion 85 is arranged to direct light towards the return portion 86 of the light guide 84 so that light transmitted through the light guide 84 travels through an optical path between the two portions 85, 86. The optical path is arranged just proximal of the flag mechanism 90. The flag 91 is dimensioned so that in the up position, it interrupts the optical path, blocking light from transmitting from the transmitting portion 85 to the return portion 86 of the light guide 84. In the other position, the flag 19 permits transmission of light between the two portions 85,86 of the light guide 84.

The light sensing means senses light transmitted through the return portion 86 of the light guide 84. If the flag 91 is up, then light is transmitted and the light sensing means generates a signal indicating that the device has not been fired. If the flag 91 is down, then the light is blocked and the sensing means generates a signal indicating that the device has been fired. The flag 19 is returned to its up position when the spent cartridge is replaced with a new cartridge containing staples.

The flag 91 may be moved by a number of means in addition to as described above. For example, as the cutting means 81 is advanced, or as a wedge or staple driver is advanced or retracted.

Referring now to FIG. 19 there is illustrated an alternative application of the optical instrument identification means of FIGS. 15 and 16. The optical identification means of this embodiment comprises dynamic code contained on a moving disposable part of an instrument. In this particular embodiment, an alternative cutting means 181 is slidable through the knife channel 80. The cutting means 181 includes a cutting blade 182 and a series of notches 183 which permit light to pass from the transmitting portion 85 to the return portion 86 of the light guide 84 when a particular notch 182 is situated in the optical path between the transmitting portion 85 and return portion 86. The series of notches may be arranged in a pattern of varying notch width which defines the instrument characteristic code.

The light sensor receives a light signal, and correspondingly transmits a signal which may be converted to a digital signal and/or interpreted by a microprocessor or CPU using means well known in the art. The signal may include, for example, the number of notches, the frequency of the notches, the length of the notches, and/or a number of different characteristic codes having distinct patterns comprised of a series of notches. These signal may be used to indicate specific instrument characteristics including instrument type as well as real time information such as instrument position (e.g., cutting means location) or speed. The code may also include an end of stroke indicator. The signal may cause the microprocessor to indicate various characteristics to a user, and/or to respond and control the instrument according to the feedback received from the instrument embodied in the signal.

Other moveable parts of the device may be used for the optical interruption means as well.

Alternatively, the optical means may include reflective surfaces arranged on, for example, the flag of FIGS. 17 and 18, or the cutting means illustrated in FIG. 19. The cutting means may have a series of reflectors arranged in a pattern on the cutting means in place of the notches. The reflectors reflect the light back towards a sensor or light guide generally on the same side of the cutting means as the light transmission means.

Several variations of this invention have been described. One specific embodiment has been illustrated in a linear cutting and stapling instrument having a cartridge for containing and dispensing staples. This invention has also been described in connection with surgical instruments having a variety of attachable, replaceable end pieces with different functions which can be distinguished by the identifications means. Of course it is anticipated by this invention that the shaft, end effector or cartridge may contain staples or other fastening means or may have different functional attributes. Accordingly it will be understood by those skilled in the art that various changes and modifications may be made in the invention without departing from its scope, which is defined by the following claims and their equivalents. Of course numerous applications and variations of this invention are possible.

We claim:

1. An surgical fastening instrument having an end effector comprising:

first and second jaw members for engaging and fastening tissue;

said first jaw member comprising a removable cartridge containing surgical fastening means; and a cartridge channel, said end effector having an electrical identification device for identifying cartridge type, wherein said identification device comprises an impedance element having a measurable, predetermined electrical characteristic.

2. The surgical fastening instrument of claim 1 wherein said identification device is contained in said first jaw member.

3. The surgical fastening instrument of claim 2 wherein stapling and firing functions are assisted by an electromechanical control means.

4. The surgical instrument of claim 3 further comprising a lockout means for preventing instrument firing when an inappropriate cartridge condition is indicated by said identification device.

5. The surgical instrument of claim 4 wherein said lockout means is controlled by internal logic of the control means.

6. The surgical fastening instrument of claim 2 further comprising indicating means for indicating to user an inappropriate cartridge condition.

7. The surgical fastening instrument of claim 1 wherein said impedance element has a predetermined electrical impedance; and wherein said impedance corresponds to an instrument characteristic.

8. The surgical fastening instrument of claim 7 wherein said impedance element comprises a resistor.

9. The surgical fastening instrument of claim 7 wherein said impedance element comprises a capacitor.

10. The surgical fastening instrument of claim 7 wherein said impedance element comprises an inductor.

11. The surgical fastening instrument of claim 10 further comprising a fuse in series with said impedance element, said fuse capable of being blown by a current applied to said fuse when said instrument is fired.

12. The surgical fastening instrument of claim 7 further comprising a fuse in series with said impedance element, said fuse capable of being blown by a current applied to said fuse when said instrument is fired.

13. The surgical fastening instrument of claim 7 wherein said impedance element is a fuse having a predetermined resistance.

14. A removable cartridge for a surgical stapling instrument comprising an electrical identification device for identifying cartridge type wherein said identification device comprises an impedance element having a measurable, predetermined electrical characteristic.

15. The cartridge of claim 14 wherein said impedance element has a predetermined electrical impedance.

16. The cartridge of claim 15 wherein said impedance element comprises a resistor.

17. The cartridge of claim 15 wherein said impedance element comprises a capacitor.

18. The cartridge of claim 15 wherein said impedance element comprises a inductor.

19. The cartridge of claim 18 further comprising a fuse in series with said impedance element, said fuse capable of being blown by a current applied to said fuse when said instrument is fired.

20. The cartridge of claim 15 further comprising a fuse in series with said impedance element, said fuse capable of being blown by a current applied to said fuse when said instrument is fired.

21. The cartridge of claim 15 wherein said impedance element is a fuse.

22. The cartridge of claim 15 wherein said impedance element comprises a fuse.

\* \* \* \* \*